United States Patent
Wall Warner et al.

(10) Patent No.: US 10,510,441 B2
(45) Date of Patent: Dec. 17, 2019

(54) DISTRIBUTED SYSTEMS FOR SECURE STORAGE AND RETRIEVAL OF ENCRYPTED BIOLOGICAL SPECIMEN DATA

(71) Applicant: GLOBAL SPECIMEN SOLUTIONS, INC., Raleigh, NC (US)

(72) Inventors: Amelia Wall Warner, Raleigh, NC (US); Mark Anthony Collins, Raleigh, NC (US)

(73) Assignee: Global Specimen Solutions, Inc., Raleigh, NC (US)

( * ) Notice: Subject to any disclaimer, the term of this patent is extended or adjusted under 35 U.S.C. 154(b) by 0 days.

(21) Appl. No.: 15/651,302

(22) Filed: Jul. 17, 2017

(65) Prior Publication Data

US 2017/0316162 A1 Nov. 2, 2017

Related U.S. Application Data

(63) Continuation of application No. PCT/US2016/062718, filed on Nov. 18, 2016.
(Continued)

(51) Int. Cl.
*G16H 10/60* (2018.01)
*G06Q 50/24* (2012.01)
(Continued)

(52) U.S. Cl.
CPC ............ *G16H 10/60* (2018.01); *G06Q 20/02* (2013.01); *G06Q 20/3821* (2013.01);
(Continued)

(58) Field of Classification Search
CPC .................... G06Q 50/22–24; G16H 50/00–80
See application file for complete search history.

(56) References Cited

U.S. PATENT DOCUMENTS

| 8,645,424 B2 * | 2/2014 | Miller | G06F 19/3418 |
| | | | 707/783 |
| 2008/0154640 A1 * | 6/2008 | DeMeyer | G16H 10/20 |
| | | | 705/2 |

(Continued)

OTHER PUBLICATIONS

PCT, International Search Report and Written Opinion for PCT/US2016/062718 dated Feb. 27, 2017.
(Continued)

*Primary Examiner* — Robert A Sorey
(74) *Attorney, Agent, or Firm* — Kilpatrick Townsend & Stockton LLP (57) ABSTRACT

The subject matter disclosed herein includes distributed systems for secure storage and retrieval of encrypted biological specimen data. According to one embodiment, the system may comprise a submission device client operable to send, to a patient record server device, a patient record; and receive, from the patient record server device, a confirmation of receipt of the patient record. The system may further comprise a patient record server device comprising a first processor and second memory, a second communications interface associated with the first processor and second memory and operable to receive, from the submission device client, the patient record; send, to the submission device client, the confirmation of receipt of the patient record; receive, from a member device client, patient profile information; determine search results based on the patient profile information; and send, to the member device client, information indicating the search results. They system may yet further comprise a member device client operable to send, to the patient record server device, the patient profile information; receive, from the patient record server device, the information indicating the search results based on the patient profile information; and receive the search results based on the information indicating the search results.

19 Claims, 5 Drawing Sheets

Related U.S. Application Data (60) Provisional application No. 62/256,759, filed on Nov. 18, 2015.

(51) Int. Cl.
*H04L 9/06* (2006.01)
*H04L 9/14* (2006.01)
*H04L 9/30* (2006.01)
*G06Q 20/02* (2012.01)
*G06Q 20/38* (2012.01)
*G16H 10/20* (2018.01)
*G06Q 20/14* (2012.01)

(52) U.S. Cl.
CPC .......... *G06Q 50/24* (2013.01); *H04L 9/0637* (2013.01); *H04L 9/14* (2013.01); *H04L 9/30* (2013.01); *G06Q 20/145* (2013.01); *G06Q 2220/00* (2013.01); *G06Q 2220/10* (2013.01); *G16H 10/20* (2018.01); *H04L 2209/56* (2013.01)

(56) References Cited

U.S. PATENT DOCUMENTS

| | | | | |
|---|---|---|---|---|
| 2012/0233141 A1* | 9/2012 | Lambie | ................ | G06F 19/321 707/706 |
| 2014/0136237 A1* | 5/2014 | Anderson | .............. | G16H 10/60 705/3 |
| 2014/0215490 A1 | 7/2014 | Mathur et al. | | |
| 2014/0316793 A1* | 10/2014 | Pruit | ...................... | G16H 10/20 705/2 |
| 2015/0205929 A1* | 7/2015 | Brama | ................ | G06F 19/3418 705/3 |
| 2015/0220928 A1 | 8/2015 | Allen | | |
| 2015/0332283 A1* | 11/2015 | Witchey | ............... | G06Q 30/018 705/3 |
| 2015/0356250 A1* | 12/2015 | Polimeni | .............. | G06F 19/322 705/3 |
| 2016/0027229 A1* | 1/2016 | Spanos | ................... | G07C 13/00 705/51 |
| 2016/0117471 A1* | 4/2016 | Belt | ..................... | G06F 19/3456 705/2 |
| 2016/0188811 A1* | 6/2016 | Wager | ................... | G06F 19/324 705/3 |
| 2016/0267605 A1* | 9/2016 | Lingham | ................ | G06Q 40/12 |
| 2016/0358253 A1* | 12/2016 | Liao | ........................ | G06Q 40/04 |
| 2017/0039330 A1* | 2/2017 | Tanner, Jr. | ............... | G06F 19/00 |
| 2017/0046698 A1* | 2/2017 | Haldenby | .......... | G06Q 20/0655 |

OTHER PUBLICATIONS

World Health Organization, International Clinical Trials Registry Platform (ICTRP), Public Disclosure of Clinical Trial Results, Apr. 14, 2015, pp. 1-4.

* cited by examiner

FIG. 5

DISTRIBUTED SYSTEMS FOR SECURE STORAGE AND RETRIEVAL OF ENCRYPTED BIOLOGICAL SPECIMEN DATA

CROSS-REFERENCE TO RELATED APPLICATION

This application is a continuation of International Patent Application Ser. No. PCT/US16/62718, filed Nov. 18, 2016, titled Distributed Systems for Secure Storage and Retrieval of Encrypted Biological Specimen Data, which claims the benefit of priority of U.S. provisional patent application No. 62/256,759 titled "BitSpecimen: A Secure Digital Encrypted Database Of Information About Specimens And Data Collected During The Course Of Clinical Trials, Research Studies, Patient Registries And Institutional And National Biobanks" filed on Nov. 18, 2015, which applications and their contents are incorporated herein by reference.

BACKGROUND OF THE INVENTION

Field of the Invention

The present invention relates to distributed systems for the storage and retrieval of encrypted biological specimen data. More specifically, it relates to a system employing blockchains in a secure peer-to-peer (P2P) networks for the storage and retrieval of encrypted data relating to biological specimens and encrypted data associated with the biological specimens.

Description of Related Art

Privacy and trust in healthcare data is of particular concern for patients, medical facilities, governments and pharmaceutical companies. In the course of clinical trials specimens are collected and data about specimens is also created as the results of analyses performed on the specimen and the patient. These highly annotated specimens are an extremely valuable resource for precision medicine, yet they are often locked away (both physically and logically) and rarely used beyond their original use. Often, privacy concerns from the patients, the medical and legal community, pharmaceutical companies, and other parties results in patients opting out of trials, limiting the use of their data and other unused data and specimens of high value. In addition, the rich data from these specimens is also locked away in siloed pharmaceutical company databases and electronic medical systems, which precludes analysis of this data through modern data analysis techniques such as data mining or crowdsourcing.

Bitcoin is an on-line cryptographic based, decentralized currency network that employs a database technology known as blockchain. Blockchain technology is the backbone of the bitcoin network and provides a tamper-proof data structure, providing a shared public ledger open to all users with access to the bitcoin network.

A blockchain is a distributed database that is secured by complex cryptography and is publically viewable, in a P2P network. Any type of data may be stored semi-publically in a blockchain. Data stored in a blockchain is signed by the user uploading the data into the blockchain. Anyone with access to the blockchain may verify that data has been uploaded by a certain user, but only the user who uploaded the data owns a private key that grants access to the data. Thus, the blockchain behaves like a database with a public header—some information is available publicly, but a specific key is required to obtain additional data from the blockchain.

The benefits of a blockchain are that it can store any type of data and keep it highly secure through a combination of encryption and private key access, but also provide limited public access to the data. These benefits make blockchains an ideal solution for storing highly sensitive data that must be shared.

SUMMARY OF THE INVENTION

The present invention employs blockchain technology in the storage of data about a biological specimen, the subject from which the specimen was obtained, healthcare data concerning the subject, and results of the analysis of the specimen, including genomic information. In embodiments of the present invention, blockchains may reside in a P2P network of computers (the exchange), managed and setup by a distributed autonomous organization (DAO). The DAO may serve all the members since the members provide value to the overall DAO by virtue of their work (e.g., adding information to their blockchain, or allowing the blockchain to be inspected and the data utilized for wider analyse).

In certain embodiments of the present invention, when a new clinical trial starts or a member wishes to provide biological specimens, the P2P network may pre-mine to create a set of empty or very short blockchain. When a patient enrolls in the trial, the empty blockchain associated with the patient may reside in the patient's individual wallet, which may act as a patient's individual biobank. As the clinical trial proceeds and the patient consents to specimen collection and analysis of such specimens, a transaction may be added to the patient's blockchain for each specimen collected or analysis performed. Such transactions may secured with the patient's private key. As more transactions and data are added to the blockchain, it becomes more complex, and those without a private key must expend additional computational resources to unlock the blockchain.

Opening up a blockchain and either adding to it, or reading it requires mining of the blockchains. When a patient wants to make his blockchain available for use by other members of the blockchain network, the patient may broadcast the fact that data is available. For example, the patient may broadcast that he is a certain ethnicity, is on certain medications, has samples banked physically, or had a single-nucleotide polymorphism analysis done to all the members of the blockchain network.

The broadcast of the patient may be picked up by the blockchain miners—individuals within the network who have an interest in obtaining that data. Miners may compete to unlock the blockchain and inspect the ledger and use the data held within it without the private key by solving the cryptographic puzzle associated with the blockchain using computational resources. The miner who wins may be rewarded with access to the data. This record of access may be appended to the patient's blockchain as a new block, which increases the security of the blockchain and the difficulty of obtaining access to it.

Each block in a blockchain may contain multiple pieces of data. For example, during a clinical trial, multiple transactions and data could be loaded into a single block, thereby reducing the computational mining cost to unlock the block chain or add to it. During the trial, only the trial sponsor could be given access to the blockchain. At the conclusion of the trial the availability of the blockchain could be broadcast to the network members, allowing any member prepared to invest the computational power to unlock it. In some embodiments, members may simply pay a monetary fee proportional to the computing time necessary to unlock a blockchain to gain access to it.

Almost any data about the patient or specimen may be added to the blockchain. For example, specimen identifiers, informed consent data, medical record, specimen chain of custody, what has happened to the specimen, results of analyses, etc. may all be added to a blockchain. Since blocks are added to a blockchain in a linear manner, the blockchain provides an overall transaction history which can be inspected. For example, if the specimen was analyzed before consent was given, or consent was revoked prior to the analysis, such legal or ethical problems would be evidenced in the sequence of the blockchain. In yet another example, if the physical specimen is to be used for analysis, the specimen owner may give permission to transfer the physical specimen to a third party, and a record of that transaction may be stored in the specimen's blockchain.

In some embodiments of present invention, a distributed system for secure storage and retrieval of encrypted biological specimen data may comprise a submission device client operable to send, to a patient record server device, a patient record; and receive, from the patient record server device, a confirmation of receipt of the patient record. The system may further comprise a patient record server device comprising a first processor and first memory, the patient record device operable to receive, from the submission device client, the patient record; send, to the submission device client, the confirmation of receipt of the patient record; receive, from a member device client, patient profile information; determine search results based on the patient profile information; and send, to the member device client, information indicating the search results. They system may yet further comprise a member device client operable to send, to the patient record server device, the patient profile information; receive, from the patient record server device, the information indicating the search results based on the patient profile information; and receive the search results based on the information indicating the search results.

In yet other embodiments of the present invention, the system may further comprise a submission device comprising a second processor and second memory, the submission device operable to execute the submission device client. The system may further comprise a member device comprising a third processor and a third memory, the memory device operable to execute the member device client.

In yet other embodiments of the present invention, the submission device client of the system may be further operable to receive a first confirmation of a patient record provider credit from the patient record server device. The patient record server device may be further operable to store the patient record provider credit in a next patient blockchain, send the first confirmation of the patient record provider credit to the submission device client, store a member device client debit in the next patient blockchain, send a second confirmation of the member device client debit to the member device client, and store an operator credit in the next patient blockchain. The member device client may be further operable to receive the second confirmation of the member device client debit from the patient record server device.

In yet other embodiments of the present invention, the patient record server device of the system may be further operable to receive, from the member device client, mined information; store the mined information in a next member blockchain; and send, to the member device client, a confirmation of storage of the mined information. The member device client may be further operable to mine the search results to extract mined information; send, to the patient record server, the mined information; and receive, from the patient record server, confirmation of the storage of the mined information.

In yet other embodiments of the present invention, the patient record server device of the system may be further operable to assign an access fee to the patient record, the patient record access fee being proportional to the amount of information stored in the patient record.

In yet other embodiments of the present invention, the submission device client of the system, in order to send the patient record, may be further operable to receive first patient record information input based on a clinical trial, send the first patient record information to the patient record server device, receive second patient record information input based on a clinical trial, and send the second patient record information to the patient record server device. The patient record server device, in order to receive the patient record, may be further operable to receive the first patient record information from the submission device client; store the first patient record information in a next blockchain; increase, in response to storing the first patient record information, the access fee associated with the patient record; receive the second patient record from the submission device client; store the second record information in the next blockchain; and increase, in response to storing the second patient record information, the access fee associated with the patient record.

In yet other embodiments of the present invention, the patient record server device of the system, in order to facilitate a clinical trial, may be further operable to receive a plurality of clinical trial patient records from a plurality of submission device clients corresponding to a plurality of clinical trial patients; group the plurality of clinical trial patient records to form a clinical trial group of patient records; restrict access, to the plurality of clinical trial patient records, to all the member device clients except for member device clients identified as clinical trial sponsor member device clients; receive information signaling the end of clinical trial; and providing access to the clinical trial patient records to other member device clients.

In some embodiments of the present invention, a method of securely storing and retrieving encrypted biological specimen data may comprise receiving a patient record from a submission device client, sending a confirmation of receipt of the patient record to the submission device client, receiving patient profile information from a member device client, determining search results based on the patient profile information, and sending information indicating the search results to the member device client.

In yet other embodiments of the present invention, the method may further comprise storing a patient record provider credit in a next patient blockchain, sending a first confirmation of the patient record provider credit to the submission device client, storing a member device client debit in the next patient blockchain, sending a second confirmation of the member device client debit to the member device client, and storing an operator credit in the next patient blockchain.

In yet other embodiments of the present invention, the method may further comprise receiving mined information from the member device client, storing the mined information in a next member blockchain, and sending a confirmation of storage of the mined information to the member device client.

In yet other embodiments of the present invention, the method may further comprise assigning an access fee to the patient record, the patient record access fee being proportional to the amount of information stored in the patient record.

In yet other embodiments of the present invention, the method may further comprise receiving first patient record information from the submission device client; storing the first patient record information in a next blockchain; increasing, in response to storing the first patient record information, the access fee associated with the patient record; receiving second patient record from the submission device client; storing the second record information in the next blockchain; and increasing, in response to storing the second patient record information, the access fee associated with the patient record.

In yet other embodiments of the present invention, receiving a plurality of clinical trial patient records from a plurality of submission device clients corresponding to a plurality of clinical trial patients; grouping the plurality of clinical trial patient records to form a clinical trial group of patient records; restricting access, to the plurality of clinical trial patient records, to all the member device clients except for member device clients identified as clinical trial sponsor member device clients; receiving information signaling the end of clinical trials; and providing access to the clinical trial patient records to other member device clients.

DETAILED DESCRIPTION

The present disclosure is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

As referred to herein, the term "computing device" should be broadly construed. In some embodiments, both the submission device 30 and member device 50 may be considered computing devices. It can include any type of mobile device, for example, a smart phone, a cell phone, a pager, a personal digital assistant (PDA, e.g., with GPRS NIC), a mobile computer with a cellular radio, or the like. A typical mobile device is a wireless data access-enabled device (e.g., an iPHONE® smart phone, a BLACKBERRY® smart phone, a NEXUS ONE™ smart phone, an iPAD™ device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or microbrowsers, which are web browsers with small file sizes that can accommodate the reduced memory constraints of wireless networks. In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on a mobile device, the examples may similarly be implemented on any suitable "computing device".

Throughout this specification, like reference numbers signify the same elements throughout the description of the figures.

When elements are referred to as being "connected" or "coupled," the elements can be directly connected or coupled together or one or more intervening elements may also be present. In contrast, when elements are referred to as being "directly connected" or "directly coupled," there are no intervening elements present.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be for example, but not limited to, an electronic, magnetic, optical, electromagnetic, infrared, or semiconductor system, apparatus, device, or propagation medium. By way of example, and not limitation, computer-readable media may comprise computer storage media and communication media.

Computer storage media includes volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and may be accessed by an instruction execution system. Note that the computer-usable or computer-readable medium can be paper or other suitable medium upon which the program is printed, as the program can be electronically captured via, for instance, optical scanning of the paper or other suitable medium, then compiled, interpreted, of otherwise processed in a suitable manner, if necessary, and then stored in a computer memory.

Communication media typically embodies computer-readable instructions, data structures, program modules or other data in a modulated data signal such as a carrier wave or other transport mechanism and includes any information delivery media. The term "modulated data signal" can be defined as a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above-mentioned should also be included within the scope of computer-readable media.

When the subject matter is embodied in the general context of computer-executable instructions, the embodiment may comprise program modules, executed by one or more systems, computers, or other devices. Generally, program modules include routines, programs, objects, components, data structures, and the like, that perform particular tasks or implement particular abstract data types. Typically, the functionality of the program modules may be combined or distributed as desired in various embodiments.

Operating environments in which embodiments of the present disclosure may be implemented are also well-known. In a representative embodiment, a computing, such as a mobile device, is connectable to a transmission functionality that varies depending on implementation. Thus, for example, where the operating environment is a wide area wireless network (e.g., a 2.5G network, a 3G network, or a 4G network), the transmission functionality comprises one or more components such as a mobile switching center (MSC) (an enhanced ISDN switch that is responsible for call handling of mobile subscribers), a visitor location register (VLR) (an intelligent database that stores on a temporary basis data required to handle calls set up or received by mobile devices registered with the VLR), a home location register (HLR) (an intelligent database responsible for management of each subscriber's records), one or more base stations (which provide radio coverage with a cell), a base station controller (BSC) (a switch that acts as a local concentrator of traffic and provides local switching to effect handover between base stations), and a packet control unit (PCU) (a device that separates data traffic coming from a mobile device). The HLR also controls certain services associated with incoming calls. Of course, the present disclosure may be implemented in other and next-generation mobile networks and devices as well. The mobile device is the physical equipment used by the end user, typically a subscriber to the wireless network. Typically, a mobile device is a 2.5G-compliant device, 3G-compliant device, or a 4G-compliant device) that includes a subscriber identity module (SIM), which is a smart card that carries subscriber-specific information, mobile equipment (e.g., radio and associated signal processing devices), a user interface (or a man-machine interface (MMI), and one or more interfaces to external devices (e.g., computers, PDAs, and the like). The mobile device may also include a memory or data store. The presently disclosed subject matter is now described in more detail.

Figure 1:
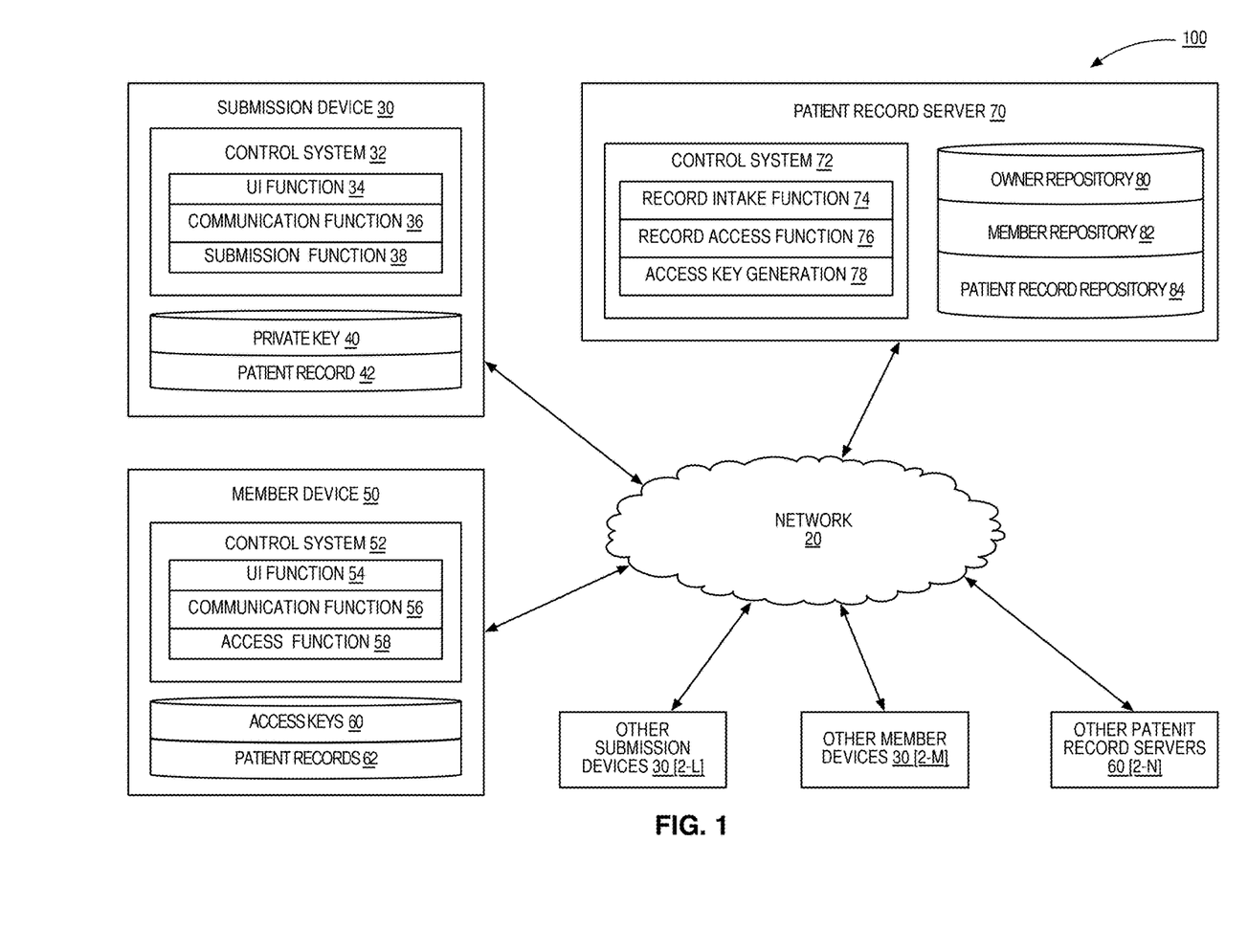
FIG. 1 is an overview system diagram illustrating an exemplary distributed system for securely storing and retrieving encrypted biological specimen data.

Referring now to FIG. 1, in some embodiments of the present invention, a distributed system for storing and retrieving encrypted biological specimen data may be comprised of a plurality of submission devices 30, a plurality of member devices 50, and a plurality of patient record server devices 70. The submission devices 30 may represent the devices used to perform submission of the patient records. The member devices 50 may represent the devices used by members (e.g., pharmaceutical companies, medical research companies, academic organizations, etc.) to access the patient records. The patient record servers 70 may represent the devices that together host the patient records in a secure and distributed manner using blockchain technology.

The submission device 30 may be comprised of a control system 32, UI Function 34, communication function 36, and a submission function 38. The private key may be stored in the key repository 40, along with the respective patient record 42 for the submission device 30. The UI function may provide the user interface controls allowing a user of the system to interact with the submission device 30. The communication function 36 may work with the communication interfaces 308 to provide communications for the submission device 30. The submission function 38 may send the patient record collected at the submission device 30 to the patient record servers 70.

The member device 50 may be comprised of a control system 52, UI Function 54, communication function 56, and an access function 58. The private key may be stored in the key repository 60, along with the respective patient records 62 for the member device 50. The UI function 54 may provide the user interface controls allowing a user of the system to interact with the member device 50. The communication function 56 may work with the communication interfaces 408 to provide communications for the member device 50. The submission function 58 may receive the patient records collected at the patient record servers 70.

The patient record servers 70 may be comprised of a control system 72, UI Function 74, communication function 76, and an access function 78. The owner repository 80 may store administrative information for the patient record servers 70. The member repository 82 may store information about the member devices 50 accessing the patient record servers 70. The patient record repository 84 may store the patient record information 42 received from the submission devices 30. The private and public keys may be stored at in the key repository 60, along with the respective patient records 62 for the member device 50. The record intake function 74 may operate to receive the patent records 42 from the submission device 30. The record access function 76 may operate to receive request for and send data in response to access to patient records 42 stored in the patient record repository 84. The communication function 77 may work with the communication interfaces 508 to provide communications for the patient record server 70. The access key generation function 78 may provide access keys to the submission devices 30 and member devices 50.

Those of ordinary skill in the art will appreciate that the network 20 is not limited by the implementations listed above. More specifically, the network 20 may be any type of network 20 suitable to allow interaction between the submission devices 30, member devices 50, and the patient record servers 70. For example, the network 20 may be a wired network, a wireless network, or any combination thereof. Further, the network 20 may include a distributed computing network, an intranet, a local-area network (LAN) and/or a wide-area network (WAN), or any combination thereof.

Figure 2A:
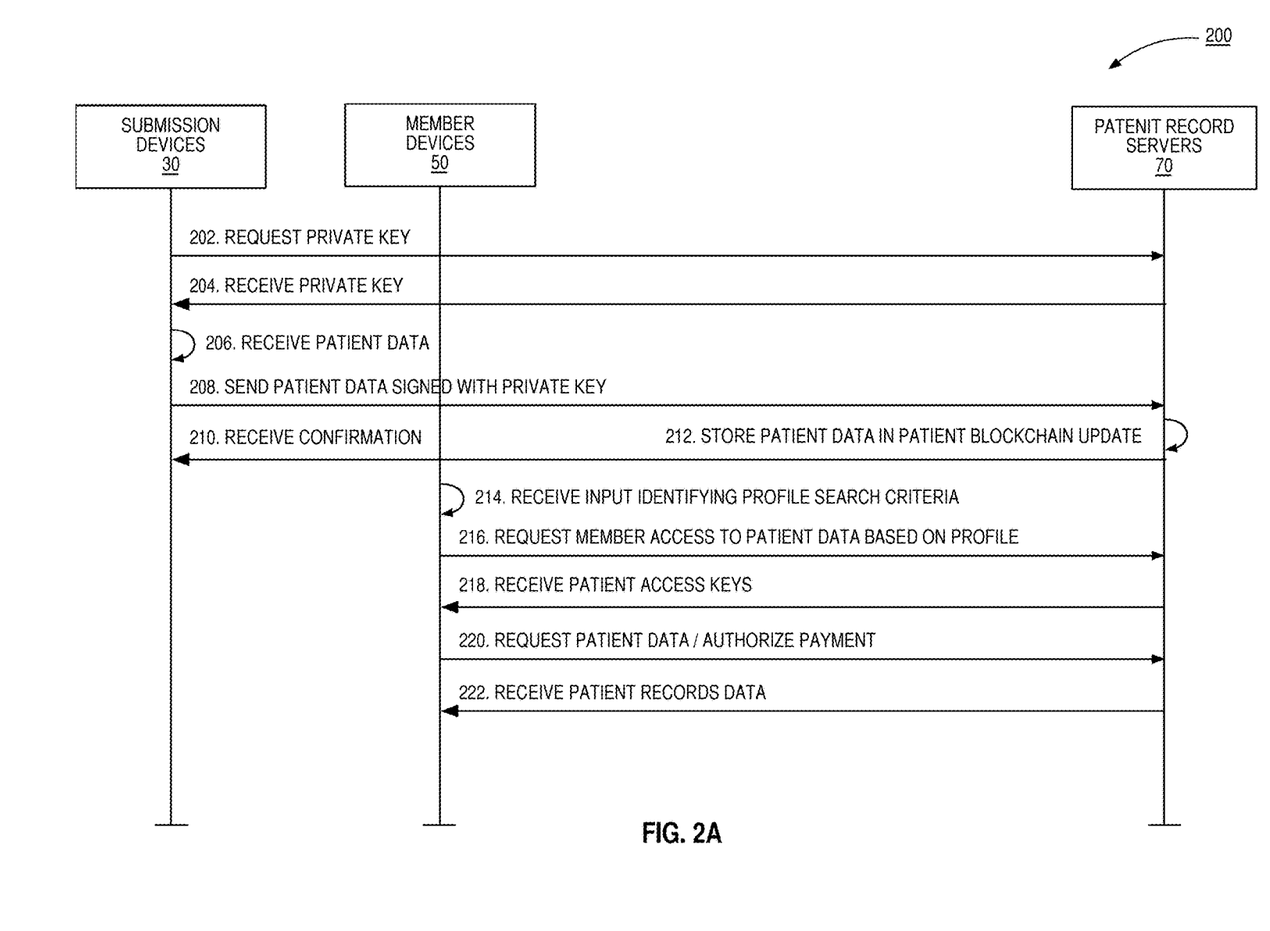
FIG. 2A is a network diagram illustrating example components and functions of a distributed system for securely storing and retrieving encrypted biological specimen data according to some embodiments of the present invention.
Figure 2B:
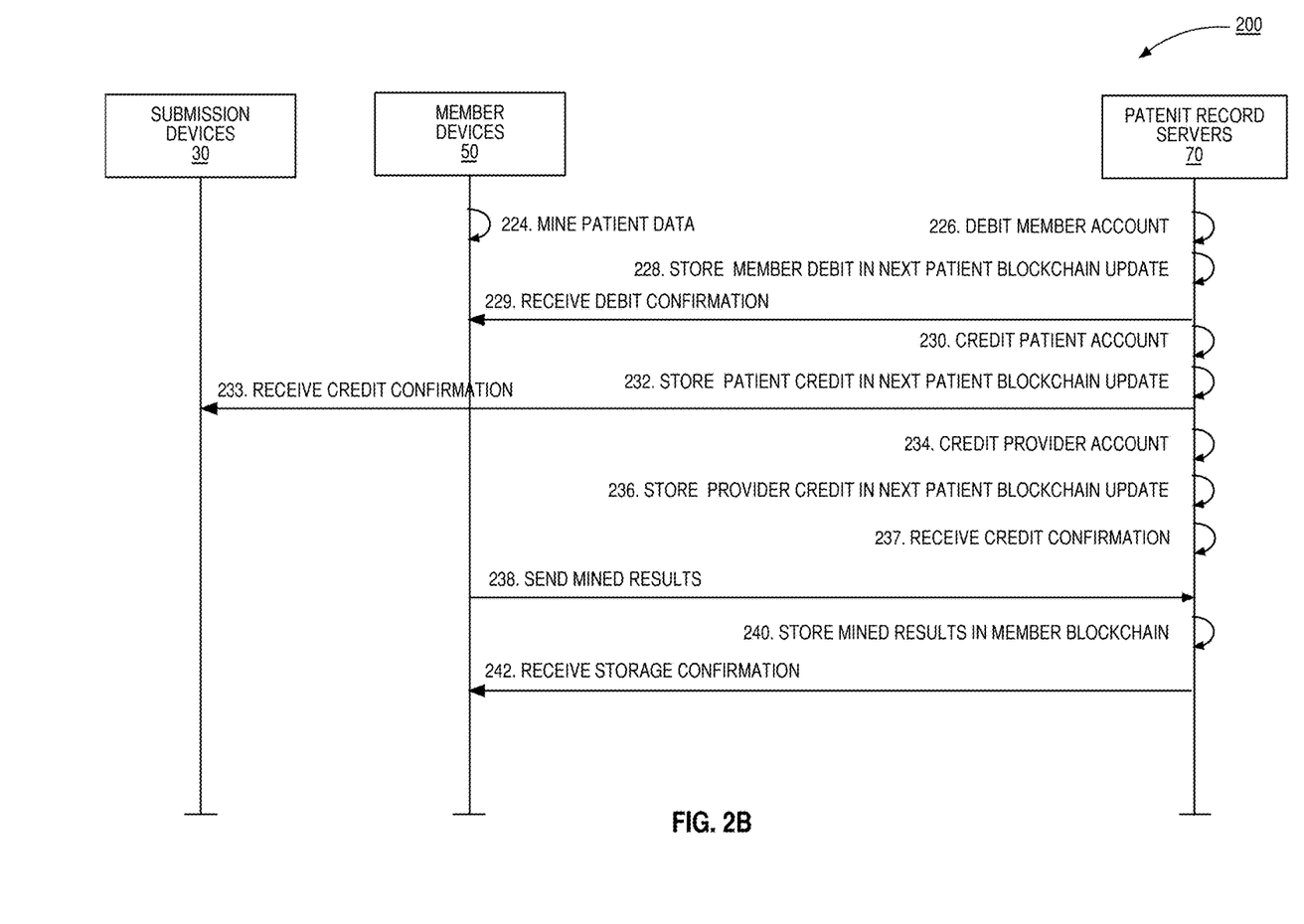
FIG. 2B is a network diagram illustrating additional example components and functions of a distributed system for securely storing and retrieving encrypted biological specimen data.

FIG. 2 depicts the network traffic on a distributed system for storing and retrieving encrypted biological specimen data according to at least one embodiment of the present invention. The submission device 30 may request 202 and receive keys 204 from the patient record servers 70. Patient data may be received 206 at the submission device 30 and sent 208 to the patient record servers 70. The patient record servers 70 may work together to add the patient records to the patient record repository 804 as part of the next blockchain 212. A confirmation of the recordation may be provided to the submission device 30. A member device 50 may receive information indicating profiles to be matched 214. The member device 50 may request access to patient data for patients matching the profile 216, and access keys may be sent to the member device 50 enabling access. Data may be requested by the member device 50 from the patient record servers 70. Payment from the member to the infrastructure operator(s) may be authorized 220. The requested data may be received 222 at the member device 50. The member device 50 may then proceed to mine the data 224. The member's account may then be debited 226 for access to the data and proof of the transaction may be recorded in the next blockchain 228. Confirmation of the member debit may be received 229 at the member device 50. The patient's account may be credited 230 for providing the data and proof of the transaction may be recorded in the next blockchain 232. Confirmation of the patient credit may be received 233 at the submission device 30. The infrastructure provider's account may be credited 234 for enabling the patient/member transaction and proof of the transaction may be recorded in the next blockchain 236. Confirmation of the provider credit may be received 237 at the submission device 30. The member device 50 may request storage of the mined results at the patient record servers 70. Confirmation of the storage may be received 242 at the member device 50.

Figure 3:
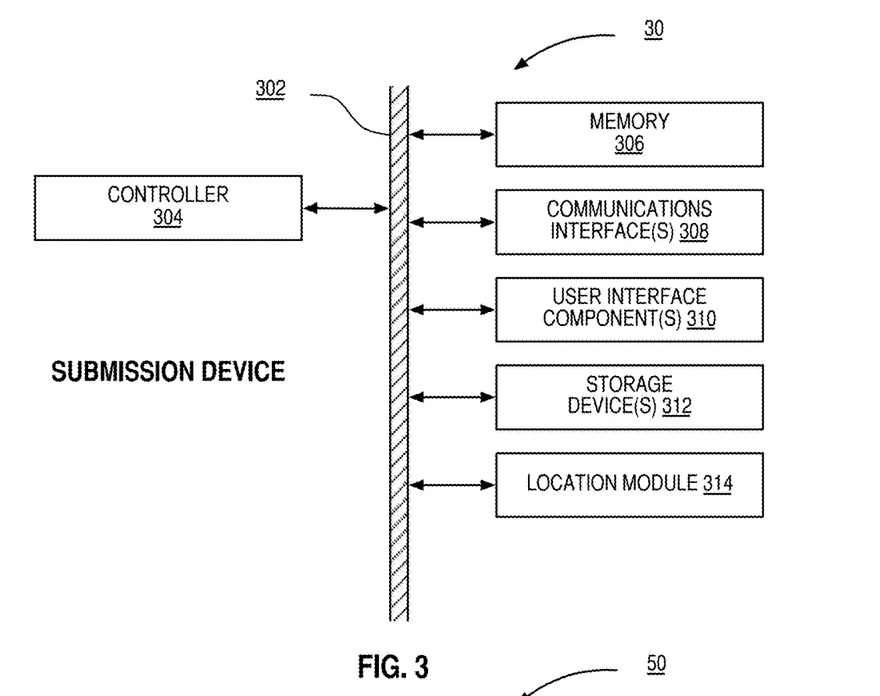
FIG. 3 is a block diagram of the hardware components comprising a submission device according to some embodiments of the present invention.

Referring now to FIG. 3, a block diagram of a submission device 30 according to at least one embodiment of the present invention is shown. As illustrated, the submission device 30 includes a controller 304 connected to memory 306, one or more communications interfaces 308, one or more user interface components 310, one or more storage devices 312, and a location module 314 by a bus 302 or similar mechanism. The controller 304 is a microprocessor, digital ASIC, FPGA, or the like. In general, the submission device 30 includes a control system 32 having associated memory 306. In this embodiment, the controller 304 is a microprocessor, and the UI function 34, communications function 36, and submission function 38 are implemented in software and stored in the memory 306 for execution by the controller 304. However, the present disclosure is not limited thereto. The aforementioned functions and engine may be implemented in software, hardware, or a combination thereof. The submission device 30 also includes a communication interface 308 enabling the submission device 30 to connect to the network 20. The one or more user interface components 310 include, for example, a touchscreen, a display, one or more user input components (e.g., a keypad), a speaker, or the like, or any combination thereof. The storage device(s) 312 is a non-volatile memory. In this embodiment, the location module 314 is a hardware component, such as a GPS receiver. However, the present invention is not limited thereto.

Figure 4:
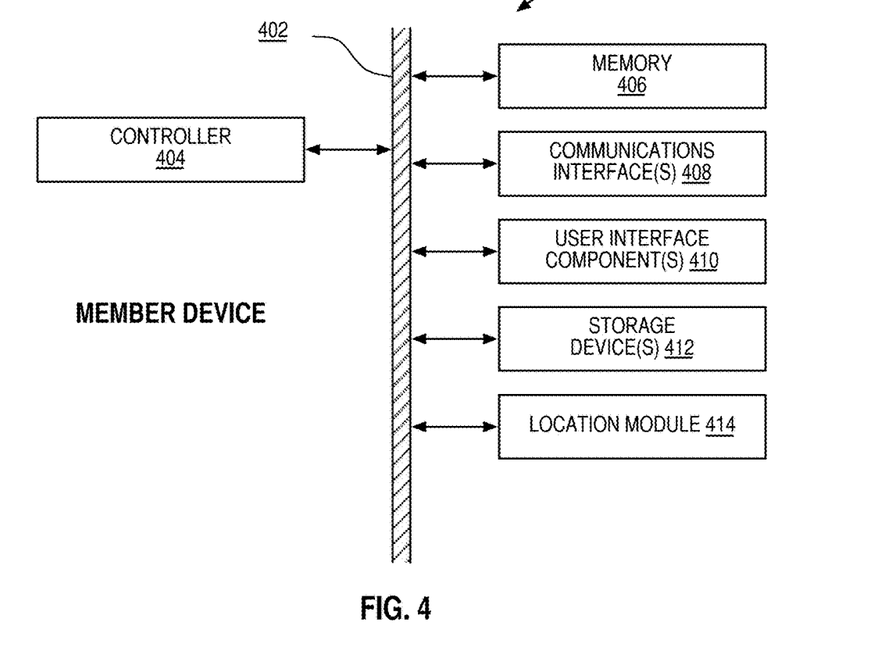
FIG. 4 is a block diagram of the hardware components comprising a member device according to some embodiments of the present invention.

FIG. 4 is a block diagram of a member device 50 according to one embodiment of the present disclosure. As illustrated, the member device 50 includes a controller 404 connected to memory 406, one or more communications interfaces 408, one or more user interface components 410, one or more storage devices 412 by a bus 402 or similar mechanism. The controller 404 is a microprocessor, digital ASIC, FPGA, or the like. In general, the member device 50 includes a control system 52 having associated memory 406. In this embodiment, the controller 404 is a microprocessor, and the and the UI function 54, communications function 56, and access function 58 are implemented in software and stored in the memory 406 for execution by the controller 404. However, the present disclosure is not limited thereto. The aforementioned functions may be implemented in software, hardware, or a combination thereof. The member device 50 also includes a communication interface 408 enabling the reference member device 50 to connect to the network 20. The one or more user interface components 410 include, for example, a touchscreen, a display, one or more user input components (e.g., a keypad), a speaker, or the like, or any combination thereof. The storage device(s) 412 is a non-volatile memory.

Figure 5:
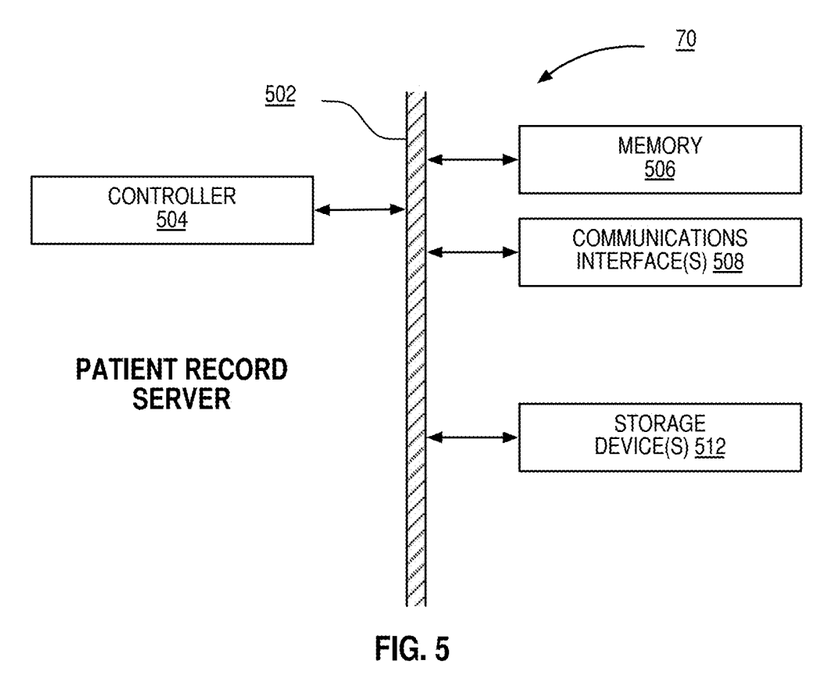
FIG. 5 is a block diagram of the hardware components comprising a patient record server according to some embodiments of the present invention.

FIG. 5 is a block diagram of a comparison server device 70 according to an embodiment of the present disclosure. As illustrated, comparison server device 70 includes a controller 504 connected to a memory 506, one or more secondary storage devices 512, and one or more communications interfaces 508 by a bus 502 or similar mechanism. The controller 504 is a microprocessor, digital Application Specific Integrated Circuit ASIC, Field Programmable Gate Array FPGA, or the like. In general, the comparison server device 70 includes a control system 72 having associated memory 506. In this embodiment, the controller 504 is a microprocessor, and the record intake function 74, record access function 76, and access key generation 78 is implemented in software and stored in the memory 506 for execution by the controller 504. However, the present disclosure is not limited thereto. The aforementioned engine may be implemented in software, hardware, or a combination thereof. Further, the owner repository 80, member repository 82, and patient record repository 84 may be stored in the one or more secondary storage devices 512. The secondary storage devices 512 are digital data storage devices such as, for example, one or more hard disk drives. The comparison server device 70 also includes a communication interface 508 enabling the comparison server device 70 to connect to the network 20.

Those skilled in the art will recognize improvements and modifications to the embodiments of the present disclosure. All such improvements and modifications are considered within the scope of the concepts disclosed herein and the claims that follow.

What is claimed is:

1. A distributed system for secure storage and retrieval of encrypted biological specimen data comprising:
    a submission device client operable to:
        send, to a patient record server device, a patient record; and receive, from the patient record server device, a confirmation of receipt of the patient record; and the patient record server device comprising:
  a first processor and first memory, the patient record server device operable to:
    create a patient blockchain that is empty at the start of a clinical trial, the patient blockchain corresponding to a patient enrolled in the clinical trial;
    receive, from the submission device client, the patient record;
    send, to the submission device client, the confirmation of receipt of the patient record;
    receive, from a member device client, patient profile information;
    determine search results based on the patient profile information;
    send, to the member device client, information indicating the search results;
    send, to the member device client, the search results based on the information indicating the search results;
    update the patient blockchain during the clinical trial by adding blocks in a linear manner;
    broadcast availability of the patient blockchain as updated during the clinical trial to network members at a conclusion of the clinical trial; and
    update the patient blockchain with a record of third party access to a physical specimen corresponding to the patient blockchain; and
  wherein the member device client is operable to:
    send, to the patient record server device, the patient profile information;
    receive, from the patient record server device, the information indicating the search results based on the patient profile information; and
    receive the search results based on the information indicating the search results.

2. The system of claim 1, further comprising:
a submission device comprising:
  a second processor and second memory, the submission device operable to:
    execute the submission device client; and
a member device comprising:
  a third processor and third memory, the memory device operable to:
    execute the member device client.

3. The system of claim 1, further comprising:
the submission device client further operable to:
  receive a first confirmation of a patient record provider credit from the patient record server device; and
the patient record server device further operable to:
  store the patient record provider credit to update the patient blockchain;
  send the first confirmation of the patient record provider credit to the submission device client;
  store a member device client debit to update the patient blockchain;
  send a second confirmation of the member device client debit to the member device client; and
  store an operator credit to update the patient blockchain; and
the member device client further operable to:
  receive the second confirmation of the member device client debit from the patient record server device.

4. The system of claim 1, further comprising:
the patient record server device further operable to:
  receive, from the member device client, mined information;
  store the mined information in a next member blockchain; and
  send, to the member device client, a confirmation of storage of the mined information; and
the member device client further operable to:
  mine the search results to extract mined information;
  send, to the patient record server, the mined information; and
  receive, from the patient record server, confirmation of the storage of the mined information.

5. The system of claim 1, further comprising:
the patient record server device further operable to:
  assign an access fee to the patient record, the access fee being proportional to an amount of information stored in the patient record.

6. The system of claim 1, further comprising:
the submission device client, in order to send the patient record, further operable to:
  receive first patient record information input based on a clinical trial;
  send the first patient record information to the patient record server device;
  receive second patient record information input based on a clinical trial; and
  send the second patient record information to the patient record server device; and
the patient record server device, in order to receive the patient record, further operable to:
  receive the first patient record information from the submission device client;
  store the first patient record information to update the patient blockchain;
  increase, in response to storing the first patient record information, the access fee associated with the patient record;
  receive the second patient record information from the submission device client;
  store the second record information to update the patient blockchain; and
  increase, in response to storing the second patient record information, the access fee associated with the patient record.

7. The system of claim 1, further comprising:
the patient record server device, in order to facilitate a clinical trial, further operable:
  receive a plurality of clinical trial patient records from a plurality of submission device clients corresponding to a plurality of clinical trial patients;
  group the plurality of clinical trial patient records to form a clinical trial group of patient records;
  restrict access, to the plurality of clinical trial patient records, to all the member device clients except for member device clients identified as clinical trial sponsor member device clients;
  receive information signaling the end of clinical trial; and
  provide access to the clinical trial group of patient records to other member device clients.

8. A patient record server device comprising:
a processor and a memory, the patient record server device operable to:
create a patient blockchain that is empty at the start of a clinical trial, the patient blockchain corresponding to a patient enrolled in the clinical trial;

update the patient blockchain during the clinical trial by adding blocks in a linear manner;
receive, from a submission device client, a patient record;
send, to the submission device client, a confirmation of receipt of the patient record;
receive, from a member device client, patient profile information;
determine search results based on the patient profile information;
send, to the member device client, information indicating the search results;
send, to the member device client, the search results based on the information indicating the search results;
broadcast availability of the patient blockchain as updated during the clinical trial to network members at a conclusion of the clinical trial; and
update the patient blockchain with a record of third party access to a physical specimen corresponding to the patient blockchain.

9. The patient record server device of claim 8, wherein the patient record server device is further operable to:
store a patient record provider credit to update the patient blockchain;
send a first confirmation of the patient record provider credit to the submission device client;
store a member device client debit to update the patient blockchain;
send a second confirmation of the member device client debit to the member device client; and
store an operator credit to update the patient blockchain.

10. The patient record server device of claim 8, wherein the patient record server device is further operable to:
receive, from the member device client, mined information;
store the mined information in a next member blockchain; and
send, to the member device client, a confirmation of storage of the mined information.

11. The patient record server device of claim 8, wherein the patient record server device is further operable to:
assign an access fee to the patient record, the access fee being proportional to an amount of information stored in the patient record.

12. The patient record server device of claim 8, wherein the patient record server device is further operable to:
receive a first patient record information from the submission device client;
store the first patient record information to update the patient blockchain;
increase, in response to storing the first patient record information, an access fee associated with the patient record;
receive a second patient record from the submission device client;
store the second patient record to update the patient blockchain; and
increase, in response to storing the second patient record, the access fee associated with the patient record.

13. The patient record server device of claim 8, wherein the patient record server device is further operable to:
receive a plurality of clinical trial patient records from a plurality of submission device clients corresponding to a plurality of clinical trial patients;
group the plurality of clinical trial patient records to form a clinical trial group of patient records;
restrict access, to the plurality of clinical trial patient records, to all the member device clients except for member device clients identified as clinical trial sponsor member device clients;
receive information signaling the end of clinical trial; and
provide access to the clinical trial group of patient records to other member device clients.

14. A method of securely storing and retrieving encrypted biological specimen data comprising:
creating, by a processor, a patient blockchain that is empty at the start of a clinical trial, the patient blockchain corresponding to a patient enrolled in the clinical trial;
updating, by the processor, the patient blockchain during the clinical trial by adding blocks in a linear manner;
receiving, by the processor, a patient record from a submission device client;
sending, by the processor, a confirmation of receipt of the patient record to the submission device client;
receiving, by the processor, patient profile information from a member device client;
determining, by the processor, search results based on the patient profile information;
sending, by the processor, information indicating the search results to the member device client;
sending, by the processor, the search results to the member device client based on the information indicating the search results;
broadcasting, by the processor, availability of the patient blockchain as updated during the clinical trial to network members at a conclusion of the clinical trial; and
updating, by the processor, the patient blockchain with a record of third party access to a physical specimen corresponding to the patient blockchain.

15. The method of claim 14, further comprising:
storing a patient record provider credit to update the patient blockchain,
sending a first confirmation of the patient record provider credit to the submission device client,
storing a member device client debit to update the patient blockchain,
sending a second confirmation of the member device client debit to the member device client, and
storing an operator credit to update the patient blockchain.

16. The method of claim 14, further comprising:
receiving mined information from the member device client,
storing the mined information in a next member blockchain, and
sending a confirmation of storage of the mined information to the member device client.

17. The method of claim 14, further comprising:
assigning an access fee to the patient record, the patient record access fee being proportional to an amount of information stored in the patient record.

18. The method of claim 14, further comprising:
receiving first patient record information from the submission device client;
storing the first patient record information to update the patient blockchain;
increasing, in response to storing the first patient record information, an access fee associated with the patient record;
receiving second patient record information from the submission device client;
storing the second patient record information to update the patient blockchain; and
increasing, in response to storing the second patient record information, the access fee associated with the patient record.

19. The method of claim 14, further comprising:
receiving a plurality of clinical trial patient records from a plurality of submission device clients corresponding to a plurality of clinical trial patients;
grouping the plurality of clinical trial patient records to form a clinical trial group of patient records;
restricting access, to the plurality of clinical trial patient records, to all the member device clients except for member device clients identified as clinical trial sponsor member device clients;
receiving information signaling the end of clinical trials; and
providing access to the clinical trial group of patient records to other member device clients.

* * * * *